Figure 1:
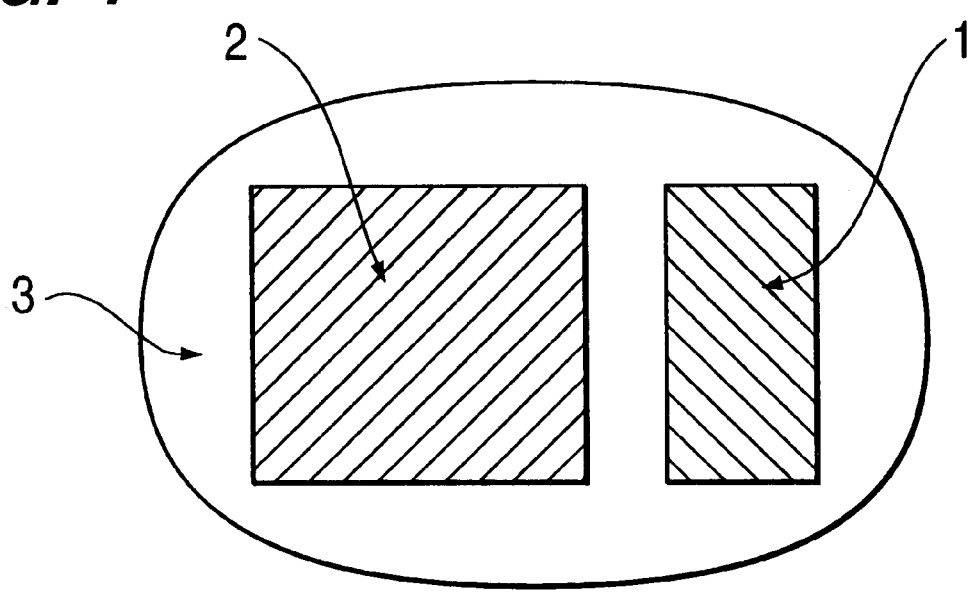

ми

United States Patent

Hille et al.

[11] Patent Number: 5,939,095
[45] Date of Patent: Aug. 17, 1999

[54] TRANSDERMAL THERAPEUTIC SYSTEM AND A PROCESS FOR THE COMBINED TRANSDERMAL APPLICATION OF PHYSOSTIGMINE AND SCOPOLAMINE FOR THE PROPHYLAXIS AND PRETREATMENT OF A POISONING CAUSED BY HIGHLY TOXIC ORGANOPHOSPHORUS NEUROTOXINS IN PARTICULAR SOMAN

[75] Inventors: Thomas Hille; Walter Müller, both of Neuwied; Bodo Asmussen, Ammersbek, all of Germany

[73] Assignee: LTS Lohmann Therapie-Systeme GmbH, Neuwied, Germany

[21] Appl. No.: 08/656,208

[22] PCT Filed: Dec. 6, 1994

[86] PCT No.: PCT/EP94/04048

§ 371 Date: Jul. 30, 1996

§ 102(e) Date: Jul. 30, 1996

[87] PCT Pub. No.: WO95/15755

PCT Pub. Date: Jun. 15, 1995

[30] Foreign Application Priority Data

Dec. 10, 1993 [DE] Germany .................... P 43 42 174

[51] Int. Cl.⁶ .................................................. A61F 13/00
[52] U.S. Cl. ........................................ 424/449; 424/448
[58] Field of Search ................................ 424/448, 449

[56] References Cited

U.S. PATENT DOCUMENTS

| 3,742,951 | 7/1973 | Zaffaroni | 128/268 |
|---|---|---|---|
| 3,797,494 | 3/1974 | Zaffaroni | 128/268 |
| 3,996,934 | 12/1976 | Zaffaroni | 128/268 |
| 4,031,894 | 6/1977 | Urquhart et al. | 128/268 |
| 4,981,858 | 1/1991 | Fisher | 514/278 |
| 5,089,267 | 2/1992 | Hille | 424/449 |
| 5,106,831 | 4/1992 | Fisher | 514/2 |
| 5,364,629 | 11/1994 | Kochinke | 424/449 |
| 5,391,375 | 2/1995 | Hille | 424/449 |

FOREIGN PATENT DOCUMENTS

| 3 315 272 | 3/1986 | Germany . |
|---|---|---|
| 3 843 239 | 2/1990 | Germany . |
| 4 115 558 | 11/1992 | Germany . |

OTHER PUBLICATIONS

Can. J. Physiol. and Pharmacol., Effects of subchronic pyridostigmine pretreatment on the toxicity of soman, J. D. Shiloff, et al. vol. 64, pp. 1047–1049, 1986.

Gov. Rep. Announce Index, Comparing the Efficacy of Physostigmine pretreatment in combination with Scopolamine versus Artane against Soman Challenge, R.P. Solana, et al, vol. 89, No. 15, abstract 942,440, 1989.

Leadbetter, "When all else fails", Chemistry in Britain, Jul. 1988 pp. 683–688.

Fleisher et al., "Dealkylation As A Mechanism For Aging of Cholinesterase After Poisoning With Pinacolyl Methylphosphonofluoridate"Biochemical Pharmacology, 1965, vol. 14, pp. 641—650.

Berry et al., "The Use of Carbamates And Atropine In The Protection of Animals Against Poisoning By 1,2,2–Trimethylpropyl Methylphosphonofluoridate"Biochemical Pharmacology, vol. 19, pp. 927—934 (1990).

*Primary Examiner*—D. Gabrielle Brouillette
*Attorney, Agent, or Firm*—Wenderoth, Lind & Ponack, L.L.P.

[57] ABSTRACT

A transdermal therapeutic system for the prophylaxis and pretreatment of a poisoning caused by highly toxic organophosphorus neurotoxins is characterized in that it has a pharmaceutical formulation with an active substance combination consisting of at least one parasympathomimetically active substance and at least one parasympatholytically active substance.

6 Claims, 1 Drawing Sheet

TRANSDERMAL THERAPEUTIC SYSTEM AND A PROCESS FOR THE COMBINED TRANSDERMAL APPLICATION OF PHYSOSTIGMINE AND SCOPOLAMINE FOR THE PROPHYLAXIS AND PRETREATMENT OF A POISONING CAUSED BY HIGHLY TOXIC ORGANOPHOSPHORUS NEUROTOXINS IN PARTICULAR SOMAN

This application is a 371 of PCT/EP94/04048, filed Dec. 6, 1994.

The present invention relates to a transdermal therapeutic system and to a process for the combined transdermal application of physostigmine and scopolamine for the prophylaxis and preliminary treatment of poisoning caused by highly toxic organophosphorus cholinesterase inhibitors, in particular soman. In particular, the present invention is to provide pharmaceutical formulations releasing suitable active substances without detrimental side effects in a controlled manner for the prophylactic treatment of poisonings caused by organophosphorus cholinesterase inhibitors.

BACKGROUND OF THE INVENTION

The group of organophosphorus cholinesterase inhibitors include certain esters of phosphoric acid derivatives, e.g., nitrostigmine (=diethyl-(4-nitrophenyl)-thiophosphate), better known under the names Parathion or E 605, but they also include tabun, as well as the phosphonic acid derivatives sarin, soman and VX.

Among other things cholinesterase-inhibiting phosphoric esters are used as insecticides in agriculture. Since they have a toxic effect on human beings too, the staff working in agriculture is subject to a basic hazard to life and limb; this is true all the more since these organic phosphoric esters can also be absorbed via the skin. As compared to insecticides, the compounds tabun, sarin, soman and VX which belong to the group of the so-called nerve warfare agents are distinguished by a particularly high toxicity. All of these compounds are more or less strong inhibitors of acetylcholinesterase, an enzyme which physiologically blocks the effect of the transmitter acetylcholine released at certain nerve endings. Most of the symptoms of poisoning caused by cholinesterase inhibitors are produced by an inundation with endogenic acetylcholine.

The basic drug therapy of such a poisoning consists in the administration of the parasympatholytic atropine, blocking the exceeding muscarinic acetylcholine effects (e.g., increase of secretion in the respiratory system, bronchospasm, inhibition of the central nervous respiratory drive). There is no suitable antagonist available to normalize the exceeding nicotinic acetylcholine actions (e.g., inhibition of the impulse transmission at the synapses of motorial nerves to the respiratory musculature and to other skeletal muscles up to a complete peripheral motor paralysis). The peripherally caused myoparesis can only be compensated by oximes, e.g., pralidoxime (PAM) or obidoxime (Toxogonin®) whose mechanism of action consists in a reactivation of the inhibited acetylcholinesterase.

However, this post-exposure therapy is not sufficient to ensure survival after poisoning with the double $LD_{50}$ of soman ($LD_{50}$=dose which is lethal for 50% of the exposed subjects). The probability of survival after a soman poisoning increases only when a pretreatment with a carbamate, e.g., pyridostigmine or physostigmine, has taken place prior to the poison exposure, and when additionally the conventional antidote-therapy with atropine and an oxime is started immediately on occurrence of the first symptoms of the poisoning. The requirement with respect to the carbamate used in the pretreatment is that it should not have significant undesired effects at the highest possible, lasting protective action, in particular it must not impair reaction capacity.

Some of the organophosphorus cholinesterase inhibitors are distinguished by the fact that they split off alkyl residues after accumulation to the acetylcholinesterase, thus stabilizing the bond ("aging"). The aged esterase inhibitor complex cannot be reactivated by oximes. In case of poisonings caused by the nerve warfare agent soman, aging already occurs after 2 to 5 minutes. The therapy with atropine and oximes can considerably be improved by a preliminary treatment with indirect parasympathomimetics, e.g., carbamic acid esters, such as pyridostigmine and physostigmine.

Carbamic acid esters inhibit the acetylcholinesterase in a manner similar to that of phosphoric acids. However, the bond is of a shorter duration and completely reversible. The fact that the carbamates inhibit part of the acetylcholinesterase, if dosed suitably, and thus remove it from the reach of the phosphoric esters and phosphonates having a stronger and prolonged inhibition may well be a decisive factor for their protective action, provided that the pretreatment started in time.

Also, the treatment of poisoning caused by phosphoric insecticides requires prompt medical care in any case. Since medical care in case of harvesters cannot always be accomplished promptly, there is a need for drugs prophylactically counteracting an intoxication. The use of carbamic acid esters for this purpose has already been described (Leadbeater, L. Chem. in Brit. 24, 683, 1988). The same applies to the effectiveness of carbamic acid esters in the pretreatment of a soman poisoning in animal experiments (Fleischer, J. H., Harris, L. W. Biochem. Pharmacol. 14, 641, 1965; Berry, W. K., Davies, D. R. Biochem. Pharmacol. 19, 927, 1970). The effective dosage of drugs to be applied prophylactically should not impair reactivity and functional capacity. However, carbamic acid esters have a low therapeutic index. As compared to pyridostigmine, an increased protective action can be achieved by physostigmine, however, the side effects are more severe.

On principle, undesired parasympathomimetic effects of the carbamates can be repressed by combinations with a parasympatholytic (e.g., atropine, scopolamine).

DE-OS 41 15 558 describes a prophylactic antidote consisting of a combination of pyridostigmine or physostigmine and N-methyl-4-piperidyl-1-phenylcyclopentane carboxylate-hydrochloride or arpenal, sycotrol, carmiphene or benactyzine, and, as an additional compelling component, a tranquilizer, i.e., diazepam or clonazepam. The undesired effects of physostigmine or pyridostigmine can therefore not be suppressed by the mentioned parasympatholytics alone, for this reason tranquilizers are additionally administered, whose side effects are problematic too.

Accordingly, it is necessary to allow the prophylactic administration of carbamic acid esters or other indirect parasympathomimetics at a dosage causing a sufficient protection against organophosphorus cholinesterase inhibitors without undesired accompanying effects.

DESCRIPTION OF THE INVENTION

It is the object of the present invention to provide a special pharmaceutical formulation of active substances for the transdermal application as a skin patch for the prophylaxis and preliminary treatment of a poisoning caused by highly toxic organophosphorus cholinesterase inhibitors, involving the lowest possible extent of side effects, with the following objectives:

continuous and uniform release of the active substances over a period of 72 h, the protective effect of the active substances shall be higher than the protective effect of atropine and reactivating oxime, undesired effects, e.g., impairment of functional capacity, shall not occur in the chosen dose.

According to the present invention this object is achieved by a transdermal therapeutic therapy-system having an active substance combination of at least one parasympathomimetically active substance and at least one parasympatholytically active substance. This solution is surprising all the more, since the present invention shows that the parasympatholytically active substance not only contributes to the protective action but also reliably suppresses the undesired effects of the parasympathomimetically active substance.

Administration forms, such as transdermal therapeutic systems, releasing active substances in a controlled manner over extended periods of time are known in the art.

In a formulation for the transdermal administration of compounds according to the present invention the pharmaceutically active substances may be contained in a matrix from which they are released in the desired gradual, constant and controlled manner. The permeability of the matrix during the release of the compound is based on diffusion. Such a system is described in German patent DE 33 15 272. This system consists of an impermeable cover layer, a specially constructed, oversaturated active substance reservoir connected therewith and made of a polymer matrix, a pressure sensitive adhesive layer connected with the reservoir and permeable to the active substance, and a protective layer which covers the pressure sensitive adhesive layer and is removed prior to use. Also, systems are possible in which the reservoir layer has a self-tackiness that is high enough for it to represent the pressure sensitive adhesive layer at the same time. German patent DE 38 43 239 describes such a system. In principle it is also possible to apply two separate TTS having one active substance each.

According to the present invention a patch system can be constructed such that it comprises two separate reservoirs for the parasympathomimetically active substance and the parasympatholytically active substance; this would mean a "Two-in-One-TTS". As an alternative, a TTS can be developed that comprises two active substances in one reservoir. When the active substances are absorbed through the skin, the person to be treated thus receives a controlled and predetermined flow of active substances.

Other suitable transdermal formulations are described in U.S. Pat. Nos. 3,742,951, 3,797,494, 3,996,934, and 4,031,894. These formulations basically consist of a back face representing one of the surfaces, an adhesive layer which is permeable to the active substance and represents the other surface, and finally a reservoir comprising the active substance between the layers forming the surfaces. Alternatively, the active substance may be comprised in a plurality of microcapsules which are distributed within a permeable adhesive layer. In any case, the active substances are continuously released from the reservoir or microcapsules through a membrane into the adhesive layer which is permeable to the active substances and which is in contact with the skin or mucosa of the person to be treated. In the case of microcapsules, the material of the capsule may also act as a membrane.

The present invention will be illustrated in more detail by means of an example:

EXAMPLE

I. Active substance-free laminate 887.0 kg acidic polyacrylate solution (50%)

10.1 kg basic methacrylate 50.4 kg triacetin 0.508 kg aluminum acetylacetonate and 37.8 kg ethanol are mixed, and a polyester film which has been rendered removable by means of siliconization is coated with this solution. After evaporation of the solvents the adhesive coating weight amounts to 120 g/m$^2$. The laminate is covered with a supporting fabric made of polyester and elastic in the longitudinal and transverse direction (active substance-free laminate).

II. Scopolamine-Containing Laminate 918.75 kg acidic polyacrylate solution (50%)

84.38 kg 1-dodecanol 3.68 kg acetylacetone 3.38 kg aceylacetonate and 18.0 kg scopolamine base are mixed, and a polyester sheet which has been rendered removable by means of siliconization is coated with this solution. After evaporation of the solvents the adhesive coating weight amounts to 150 g/m$^2$. The laminate is covered with a polyester sheet having a thickness of 23 $\mu$m.

III. Physostigmine-Containing Laminate 542.2 kg acidic polyacrylate solution (50%)

125.8 kg 1-dodecanol 83.3 kg physostigmine 83.3 kg basic methacrylate 16.6 kg aluminum acetylacetonate and 166.6 kg ethanol are mixed, and a PE-sheet which has been rendered removable by means of siliconization is coated with this solution. After evaporation of the solvents the adhesive coating weight amounts to 240 g/m$^2$. The following narrow rolls are cut:

PE-sheet with siliconization: 87 mm in width (I)

Active substance-free laminate: 87 mm in width (II)

Scopolamine-containing laminate: 15 mm in width (III)

Physostigmine-containing laminate: 50 mm in width (IV)

The removable siliconized PE-sheets are removed from the scopolamine and physostigmine-containing laminates (II and III), and the adhesive side of rectangles having a size of 15×50 mm$^2$ and 50×50 mm$^2$ are transferred on the middle of and parallel to the edges of the PE-film (I).

Then, the removable PE-sheet I is removed from the active substance-free laminate (II), and the adhesive side of the laminate (II) is laminated along the edges over the web (I) provided with the rectangles. The systems are separated by means of an oval punching tool.

BRIEF DESCRIPTION OF DRAWING

FIG. 1 shows the top view of the systems after removal of the protective layer.

1. represents a reservoir portion with scopolamine
2. represents a reservoir portion with physostigmine
3. represents an active substance-free adhesive edge.

The controlled release of the active substances both into physiological saline and through excized rodent skin are shown in Tables 1 and 2.

TABLE 1

| Accumulated release after | 2 h | 4 h | 8 h | 24 h |
|---|---|---|---|---|
| Scopolamine [mg/cm$^2$] | 0.1 | 0.14 | 0.20 | 0.33 |
| Physostigmine [mg/cm$^2$] | 0.5 | 0.69 | 1.02 | 1.71 |

Table 1:

In-vitro-liberation of scopolamine and physostigmine

Release apparatus: rotating cylinder acc. to US PXXII

Release medium: physiological saline solution

Content determination by means of HPLC

TABLE 2

| Accumulated release after | 8 h | 24 h | 48 h | 72 h |
|---|---|---|---|---|
| Scopolamine [µg/2.54 cm$^2$] | 5.6 | 67.6 | 200 | — |
| Physostigmine [µg/2.54 cm$^2$] | 95 | 850 | 2160 | 3430 |

Table 2:

Penetration rate of scopolamine and physostigmine

Release apparatus: Franz-Cell (type of skin: guinea pig)

Release medium: physiological saline solution

Determination of content by means of HPLC.

The results shown in Table 2 prove the functional performance of the transdermal therapeutic system according to the present invention over a period of two and three full days, respectively.

Potency test based on animal experiments:

The protective effect of pyridostigmine and physostigmine alone and combined with scopolamine was tested on the basis of a soman poisoning in guinea pigs. 24 hours before the soman load, 6 to 10 animals received a pyridostigmine (3 cm$^2$/kg) or physostigmine (1.5 cm$^2$/kg) skin patch. After a 24-hour application of the physostigmine skin patch, plasma concentrations of 0.9±0.3 ng/ml (average value ±SEM; n=4) were measured. When the larger pyridostigmine skin patch was applied, the cholinesterase activity in the total blood was inhibited by 38±4%, in case of the smaller physostigmine skin patch by 48±10%. In order to test the additional protective action of scopolamine either a commercial transdermal therapeutic system (Scopoderm® TTS) was used, or osmotic minipumps (Alzet®) having a release rate of 9 to 10 ng scopolamine hydrobromide per kg of body weight and hour were implanted subcutaneously into the animals. The results obtained after application of the pyridostigmine and physostigmine skin patches and a soman load of 1.5 LD$_{50}$ intramuscular are shown in Table 3.

The physostigmine pretreatment is not only effective in case of a poisoning by soman but also in case of a sarin poisoning: after a transdermal pretreatment with physostigmine-Scopoderm®-TTS and a load of 1.5 LD$_{50}$ sarin, 9 out of 10 guinea pigs survived without an additional post-exposure therapy.

The efficacy of the physostigmine pretreatment with and without scopolamine against soman was determined in an additional test series on guinea pigs, wherein an additional post-exposure therapy was applied using atropine sulfate and obidoxime chloride, based on the efficacy index (protective ratio=quotient of LD$_{50}$ with treatment and LD$_{50}$ without treatment) (Table 4).

TABLE 3

Protective action of different kinds of preliminary treatments in guinea pigs against a load of 1.5 LD$_{50}$ soman IM, without an additional post-exposure therapy

| Pretreatment | Lethality rate (24 h) |
|---|---|
| no | 10/10 |
| pyridostigmine transdermally (3 cm$^2$/kg) | 6/6 |
| pyridostigmine transdermally (1.5 cm$^2$/kg) + Alzet ®-scopolamine 10 ng/kg$^{-1}$h$^{-1}$ | 5/6 |
| pyridostigmine transdermally (1.5 cm$^2$/kg) | 6/20 |
| pyridostigmine transdermally (1.5 cm$^2$/kg) + Alzet ®-scopolamine 9 ng kg$^{-1}$h$^{-1}$ | 0/10 |
| physostigmine transdermally (1.5 cm$^2$/kg) + Scopoderm ®-TTS | 1/10 |

TABLE 4

Efficacy of a physostigmine or combined physostigmine-scopolamine-pretreatment in guinea pigs against a soman load and additional post-exposure therapy with atropine sulfate and obidoxime chloride (in each case 10 mg/kg body weight IM, 1 min. after soman).

| Pretreatment | Efficacy index*) (fiduciary limits) |
|---|---|
| physostigmine transdermally (1.5 cm$^2$/kg) | 3.45 (3.00; 3.95) |
| pyridostigmine transdermally (1.5 cm$^2$/kg) + Alzet ®-scopolamine 4.5 ng kg$^{-1}$h$^{-1}$ | 3.70 (3.65; 4.50) |

$$*) \text{ efficacy index} = \frac{LD_{50} \text{ with treatment}}{LD_{50} \text{ without treatment}}$$

In test series using two different physostigmine formulations, the combined pretreatment with transdermal physostigmine and Scopoderm®-TTS without post-exposure therapy resulted in efficacy indices of 2.11 (1.71; 2.60) and 2.27 (1.86; 2.79), respectively.

The pharmocokinetics of transdermally administered physostigmine and scopolamine was tested on pigs. Within a period of 5 to 6 h, the plasma concentration rose to a level which lasted for 72 h. In order to examine the effectiveness against an intravenous soman load in pigs, physostigmine skin patches (0.5 cm$^2$/kg) were used which resulted in plasma concentrations of 1.1±0.1 ng/ml (16±3% inhibition of the cholinesterase activity in the total blood) after 48 h. The Scopoderm®-TTS caused scopolamine concentrations in the plasma of 0.18±0.06 ng/ml (n=9) after 24 h. The following results (Table 5) were obtained for a load of 2.5 LD$_{50}$ soman without additional post-exposure therapy:

TABLE 5

Protective action of the physostigmine and physostigmine-scopolamine pretreatment in pigs against a load of 2.5 LD$_{50}$ soman IV, without additional post-exposure therapy

| Pretreatment | Lethality rate | Mean recovery time *) (min.) |
|---|---|---|
| Scopoderm ®-TTS | 4/4 | — |
| Physostigmine transdermally (0.5 cm$^2$/kg) | 1/4 | 146 |
| Physostigmine transdermally (0.5 cm$^2$/kg) + Scopoderm ®-TTS | 2/5 | 29 |

*) Recovery time = period until the surviving animals are able to stand and walk.

When the pigs were not subjected to 2.5 LD$_{50}$ but to 4 LD$_{50}$ soman IV after the transdermal physostigminescopolamine-pretreatment, and when a post-exposure therapy was carried out 20 s later (0.5 mg atropine sulfate and 3 mg obidoxime chloride/kg body weight, IM), 3 out of 5 animals survived, with the surviving animals having higher physostigmine and scopolamine concentrations than the dead ones. When the post-exposure therapy additionally comprised loprazolam (0.2 mg/kg, IM) all of the 5 animals survived, however, recovery of 2 animals was insufficient, exemplifying the disadvantages of the benzodiazepine administration.

Clinical Tolerance Studies

The tolerance of physostigmine skin patches was tested with 11 voluntary test persons (age 29±2 years) under double-blind-conditions as against placebo and additional use of Scopoderm® TTS. With the physostigmine concentrations in the plasma amounting to 0.3±0.1 ng/ml after 48 h, and the scopolamine concentrations amounting to 0.07±0.01 ng/ml, scopolamine proved to be effective in suppressing the undesired effects caused by physostigmine, in particular nausea and vomiting. Statistically significant changes in behavior and performance could not be detected in case of the combined physostigmine-scopolamine-treatment. Accordingly, the object according to the present invention is achieved, i.e., to develop an administration form comprising at least one parasympathomimetically active substance and at least one parasympatholytically active substance, without occurrence of the side effects typical for these substances.

We claim:

1. A method for the prophylaxis or pretreatment of poisoning caused by toxic organophosphorus neurotoxins, which comprises the transdermal therapeutic application of a patch to a patient in need thereof of an effective amount of an active substance combination of at least one parasympathomimetically active substance and at least one parasympatholytically active substance, at least one of said active substances being in a form acting as a depot.

2. A method according to claim 1 wherein the parasympatholytically active substance is selected from the group consisting of the tropane alkaloids, a pharmaceutically acceptable salt thereof and a racemic mixture thereof.

3. A method according to claim 1 wherein the parasympathomimetically active substance is an indirect parasympathomimetic.

4. A method according to claim 3 wherein the parasympathomimetically active substance is an acetylcholinesterase inhibitor selected from the group consisting of physostigmine, heptylphysostigmine, neostigmine, pyridostigmine, galanthamine, tetrahydroacridine, velnacridine, their pharmaceutically acceptable salts and racemic mixtures.

5. A method according to claim 1 wherein separate areas of matrix or reservoir portions for the parasympathomimetically active substance and for the parasympatholytically active substance in a therapeutic patch are used.

6. A method according to claim 1 wherein physostigmine and/or a pharmaceutically acceptable salt thereof is used as parasympathomimetically active substance and that scopolamine and/or a pharmaceutically acceptable salt thereof is used as parasympatholytically active substance.

* * * * *